United States Patent [19]
Inukai et al.

[11] Patent Number: 5,830,148
[45] Date of Patent: Nov. 3, 1998

[54] SYSTEM AND METHOD FOR EVALUATING THE AUTONOMIC NERVOUS SYSTEM OF A LIVING SUBJECT

[75] Inventors: Hidekatsu Inukai, Nagoya, Japan; Hiroshi Sakai, deceased, late of Komaki, Japan, by Hiroko Sakai, legal heir

[73] Assignee: Colin Corporation, Komaki, Japan

[21] Appl. No.: 867,817

[22] Filed: Jun. 3, 1997

[51] Int. Cl.⁶ .................................................. A61B 5/02
[52] U.S. Cl. .................... 600/481; 600/513; 600/492; 600/493
[58] Field of Search .................................. 600/481, 485, 600/492–494, 508, 509, 513

[56] References Cited

U.S. PATENT DOCUMENTS

| | | | |
|---|---|---|---|
| 4,832,038 | 5/1989 | Arai et al. | 600/483 |
| 5,131,391 | 7/1992 | Sakai et al. | |
| 5,299,119 | 3/1994 | Kraf et al. | 600/509 |

FOREIGN PATENT DOCUMENTS

| | | |
|---|---|---|
| 638281 | 2/1995 | European Pat. Off. . |
| 774234 | 5/1997 | European Pat. Off. . |
| 8-000583 | 1/1996 | Japan . |
| 9-122087 | 5/1997 | Japan . |
| WO-A2-96-08992 | 5/1996 | WIPO . |

*Primary Examiner*—William E. Kamm
*Assistant Examiner*—George R. Evanisko
*Attorney, Agent, or Firm*—Oliff & Berridge, PLC

[57] ABSTRACT

A system and method evaluates the autonomic nervous system of a living subject based on the high frequency components present in the fluctuations of the living subject's pulse cycle and on the low frequency components present in the fluctuations of the living subject's blood pressure. The autonomic nervous system evaluation system includes an electrocardiographic waveform determiner that detects an electrocardiographic waveform of the living subject. A pulse cycle determining circuit determines a pulse cycle of the living subject based on the electrocardiographic waveform. A blood pressure estimating circuit estimates the living subject's blood pressure based on time differences between predetermined periodic points on the electrocardiographic waveform and predetermined periodic points on corresponding pulse waves. An autonomic nervous system evaluation circuit evaluates the autonomic nervous system of the living subject based on the frequency content of fluctuations present in the blood pressure and pulse cycle of the living subject.

29 Claims, 5 Drawing Sheets

SYSTEM AND METHOD FOR EVALUATING THE AUTONOMIC NERVOUS SYSTEM OF A LIVING SUBJECT

BACKGROUND OF THE INVENTION

1. Field of Invention

This invention relates to medical diagnostic systems. More specifically, this invention is directed to a system and method for evaluating the autonomic nervous system of a living subject.

2. Description of Related Art

The pulse cycle and blood pressure of a living subject exhibit fluctuations over time. A frequency analysis of these fluctuations reveal that the fluctuations in both the pulse cycle and the blood pressure of a living subject contain a high frequency band with a peak at a frequency that is approximately the same as the respiratory frequency of the living subject. In addition, the frequency analysis reveals a low frequency band with a peak at a frequency that is approximately ¼ to ⅓ of the respiratory frequency of the living subject.

Thus, the frequency of the fluctuations exhibited by the pulse cycle and the blood pressure of a living subject can be analyzed and used to evaluate the autonomic nervous system of a living subject. Specifically, the high frequency components present in the fluctuations of the living subject's pulse cycle can be used to evaluate the parasympathetic nervous system. The low frequency components present in the fluctuations of the living subject's blood pressure can be used to evaluate the sympathetic nervous system.

To evaluate the autonomic nervous system based on the fluctuations exhibited by the living subject's pulse cycle and the living subject's blood pressure, the living subject's pulse cycle and blood pressure must be continuously measured. However, it is difficult to continuously measure the blood pressure of a living subject.

One device for continuously measuring the blood pressure of a living subject is a tonometric-type automatic blood pressure measurement device. This device continuously measures the blood pressure of a living subject by applying pressure to a radial artery of the living subject. However, this type of device is complex and expensive.

SUMMARY OF THE INVENTION

This invention provides an inexpensive and simple system and method for evaluating the autonomic nervous system of a living subject. The system and method of this invention evaluates the autonomic nervous system of a living subject based on the high frequency components present in the fluctuations of the living subject's pulse cycle and on the low frequency components present in the fluctuations of the living subject's blood pressure.

The autonomic nervous system evaluation system of this invention provides an electrocardiographic waveform determiner that detects an electrocardiographic waveform generated by the change in electric potential of the living subject's cardiac muscle. In addition, a volume pulse wave detector detects a pulse wave of the living subject.

A pulse cycle determining circuit determines a pulse cycle of the living subject based on the electrocardiographic waveform. A time-difference determining circuit determines time differences between predetermined periodic points on the electrocardiographic waveform and predetermined periodic points on corresponding pulse waves detected by the volume pulse wave detector. A blood pressure estimating circuit estimates the living subject's blood pressure based on the time differences determined by the time-difference determining circuit. An autonomic nervous system evaluation circuit evaluates the autonomic nervous system of the living subject based on the high frequency components present in the fluctuations of the determined pulse cycle of the living subject, and on the low frequency components present in the fluctuations of the determined blood pressure of the living subject.

These and other features and advantages of this invention are described and are apparent from the following detailed description of the preferred embodiments.

BRIEF DESCRIPTION OF THE DRAWINGS

The preferred embodiments of this invention will be described in detail, with references to the following figures, wherein.

DETAILED DESCRIPTION OF PREFERRED EMBODIMENTS

Figure 1:
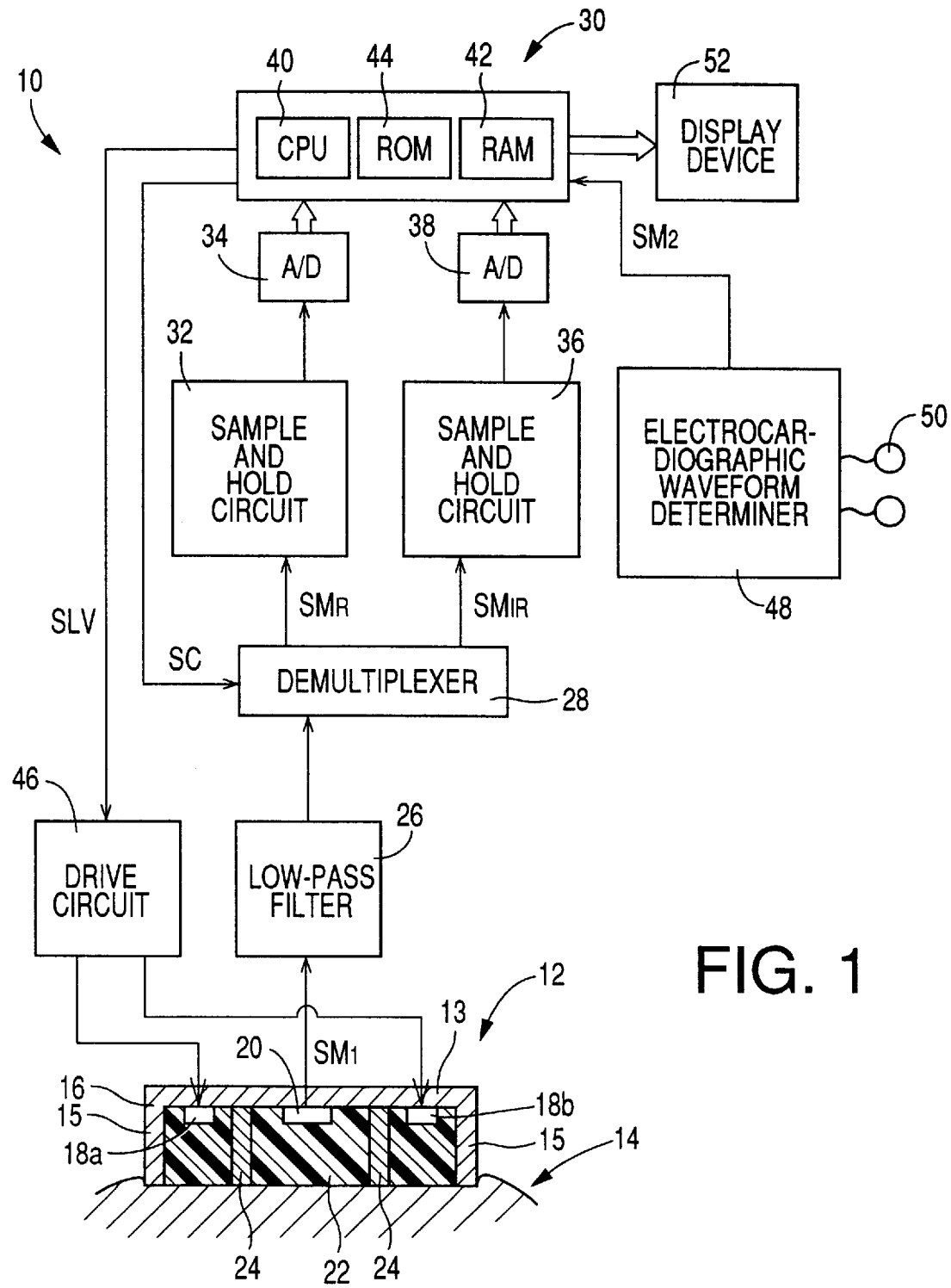
FIG. 1 is a block diagram of an oxygen saturation measurement device incorporating the autonomic nervous system evaluation system of this invention.

FIG. 1 shows an oxygen saturation level measuring device 10 that incorporates the autonomic nervous system evaluation system of this invention. The device 10 includes a photoelectric pulse wave detector 12 that is tightly attached to the surface 14 of a living subject. The pulse wave detector 12 is preferably attached to the tip of a finger of the living subject, preferably with bands.

The photoelectric pulse wave detector 12 has a container-like housing 16 that has a top portion 13, side portions 15 and an open bottom. A photodetector 20 is attached to the bottom surface of the top portion 13. The photodetector 20 is preferably centered on the top portion 13 of the housing 16.

A first group of light emitters 18a and a second group of light emitters 18b are attached to the bottom surface of the top portion 13 alternately around the photodetector 20. The first group of light emitters 18a preferably emit red light at a wavelength of approximately 660 nm and the second group of light emitters 18b preferably emit infrared light at a wavelength of approximately 800 nm.

A transparent resin 22, preferably acrylic resin, fills the inside of the housing 16 and encases the photodetector 20 and light emitters 18a and 18b. A light shield 24, preferably a metal plate, is positioned inside the housing 16 to shield the photodetector 20 from light reflected directly towards the photodetector 20 by the surface 14.

In operation, the light emitters 18a and 18b are turned on and off in an alternating fashion at a predetermined frequency. Thus, only one of the two light emitter groups 18a and 18b is on at any given time. Light emitted by either the light emitters 18a or the light emitters 18b impinges on and penetrates into the surface 14 of the living subject and is dispersed by the hemoglobin in the capillaries of the living subject. A portion of the dispersed light is detected by the photodetector 20.

Although the first group of light emitters 18a emit light at a preferred wavelength of 660 nm, other wavelengths may be used so long as, at the selected wavelength, the absorption coefficient of oxidized hemoglobin is substantially different than the absorption coefficient of reduced hemoglobin.

The photodetector 20 detects a portion of the light dispersed by capillaries that are close to the surface 14 of the living subject and outputs a pulse wave signal $SM_1$ whose magnitude is proportional to the amount of light detected. The pulse wave signal $SM_1$ is input to a demultiplexer 28 via a low-pass filter 26.

The low-pass filter 26 removes high frequency noise from the pulse wave signal $SM_1$. If necessary, an amplifier (not shown) may be used between the photodetector 20 and the low-pass filter 26.

The demultiplexer 28 is synchronized with the pulse wave detector 12. Thus, the demultiplexer 28 alternately supplies red light signals $SM_R$, via a sample and hold circuit 32 and an A/D converter 34, and infrared signals $SM_{IR}$, via a sample and hold circuit 36 and an A/D converter 38, to an input/output port of an electronic control device 30. The sample and hold circuits 32 and 36 hold the current $SM_R$ and $SM_{IR}$ signals until the previous $SM_R$ and $SM_{IR}$ are processed by the electronic control device 30.

The oxygen saturation level measurement device 10 also includes an electrocardiographic waveform determiner 48. The electrocardiographic waveform determiner 48 continuously detects an electrocardiographic waveform that indicates the change in electric potential of the living subject's cardiac muscle. The electrocardiographic waveform determiner 48 determines the electrocardiographic waveform from signals supplied by electrocardio electrodes 50. The electrocardio electrodes 50 are placed at predetermined positions on the living subject. The electrocardiographic waveform determiner 48 supplies the electrocardiographic waveform to the electronic control device 30 as an electrocardiographic signal $SM_2$.

The electronic control device 30 preferably includes a central processing unit (CPU) 40, a read-only memory (ROM) 44, a random-access memory (RAM) 42 and an input/output (I/O) port. The CPU 40 processes input signals according to control programs pre-stored in the ROM 44 by using the RAM 42 as temporary storage. In addition, the CPU 40 outputs signals to an display device 52.

The display device 52 is suitably a liquid crystal display. In addition, the display device 52 may be suitably formed from light emitting elements, e.g., light emitting diodes. Alternatively, the display device 52 may be a printer.

When a measurement is initiated, the CPU 40 sends drive signals SLV to the light emitters 18a and 18b of the pulse wave detector 12 via the drive circuit 46. As discussed above, the CPU 40 controls the light emitters 18a and 18b to alternately emit light.

The CPU 40 also routes the signal $SM_R$ to the sample and hold circuit 32 and the signal $SM_{IR}$ to the sample and hold circuit 36 by sending a switching signal SC to the demultiplexer 28. In addition, the CPU 40 determines a level of hemal oxygen saturation in the living subject's blood based on the amplitudes of the signals $SM_R$ and $SM_{IR}$. The CPU 40 determines the level of hemal oxygen saturation using predetermined programs stored in the ROM 44. One method of determining the level of hemal oxygen saturation is disclosed in U.S. Pat. No. 5,131,391.

Figure 2:
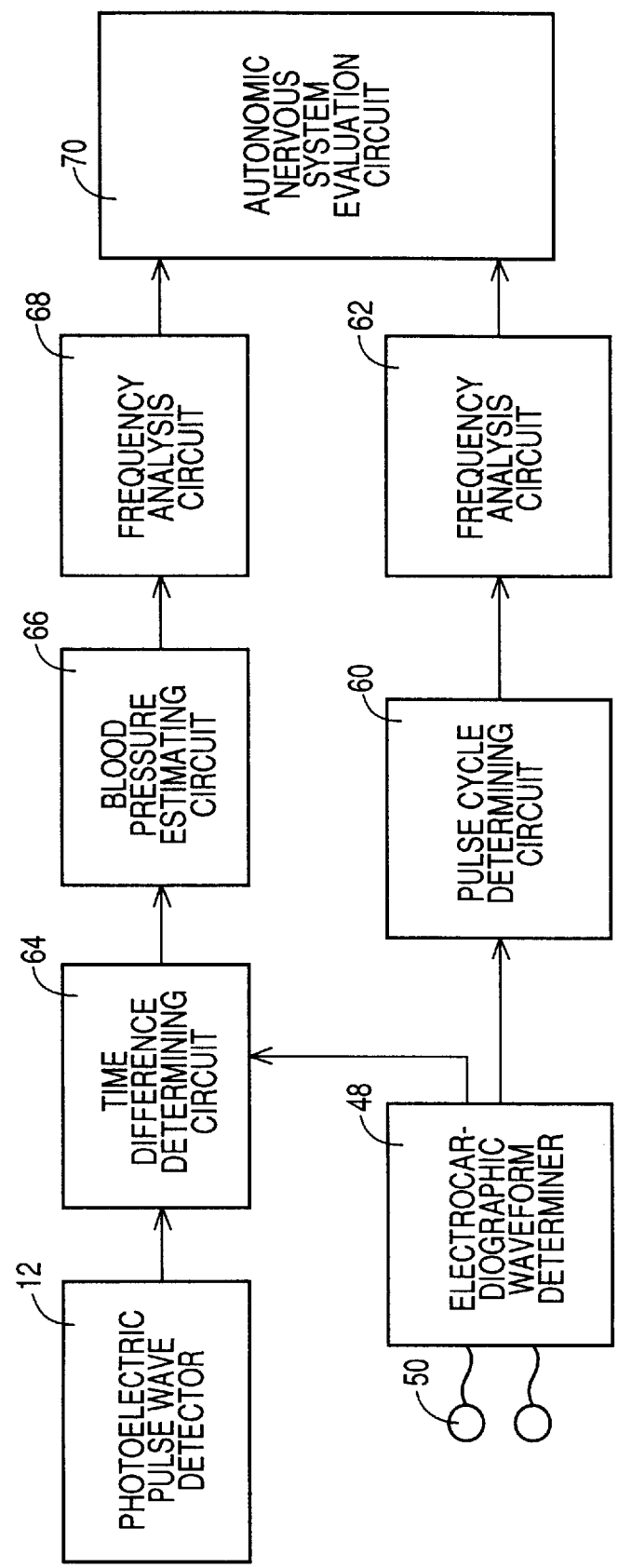
FIG. 2 is a block diagram of an electronic control device of the oxygen saturation measurement device of FIG. 1.

FIG. 2 shows the control functions of the electronic control device 30 of the oxygen saturation measurement device 10.

Figure 3:
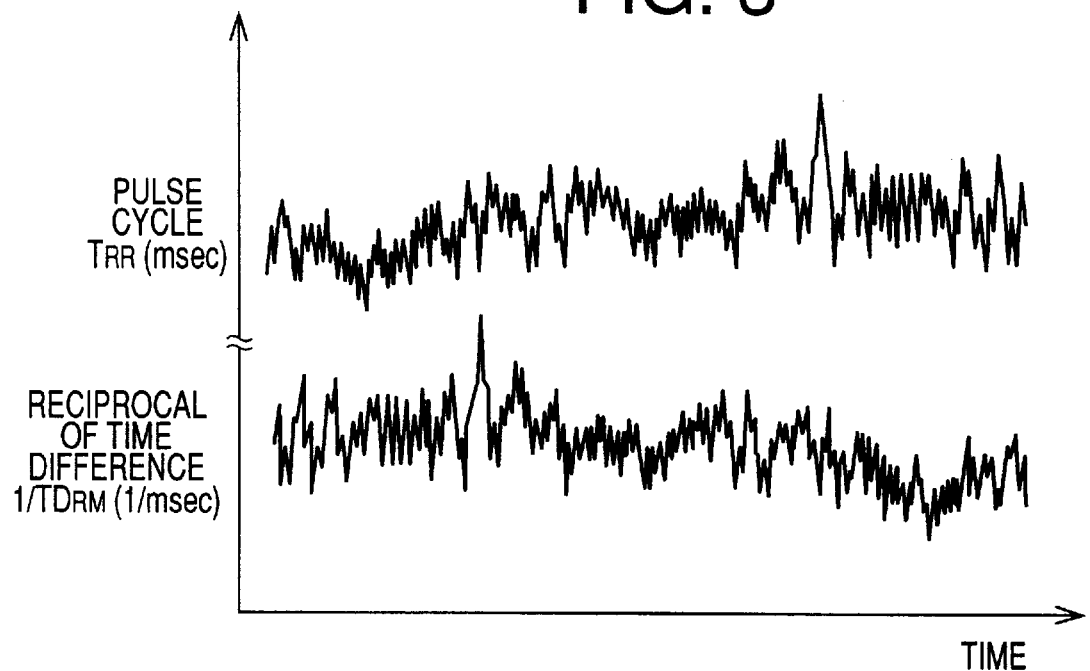
FIG. 3 is a graph showing fluctuations of a pulse cycle and fluctuations of the reciprocal of a time difference $TD_{RM}$ determined by the autonomic nervous system evaluation system of this invention.

A pulse cycle determining circuit 60 continuously detects a pulse cycle $T_{RR}$ of the living subject from the electrocardiographic waveform determined by the electrocardiographic waveform determiner 48. The pulse cycle determining circuit 60 determines the living subject's pulse cycle by measuring the time difference between successive occurrences of a predetermined periodic point on the electrocardiographic waveform. The pulse cycle determining circuit 60 preferably detects the pulse cycle $T_{RR}$ of the living subject from successive occurrences of an R point on the electrocardiographic waveform of the living subject. The pulse cycle $T_{RR}$ determined by the pulse cycle determining circuit 60 fluctuates over time, as shown in FIG. 3.

A frequency analysis circuit 62 receives the continuously detected pulse cycle from the pulse cycle determining circuit 60 and determines the frequency content of the fluctuations exhibited by the pulse cycle $T_{RR}$. The frequency analysis circuit 62 preferably uses fast Fourier transform techniques or auto-regressive techniques to analyze the frequency content of the fluctuations in the pulse cycle $T_{RR}$.

Figure 4:
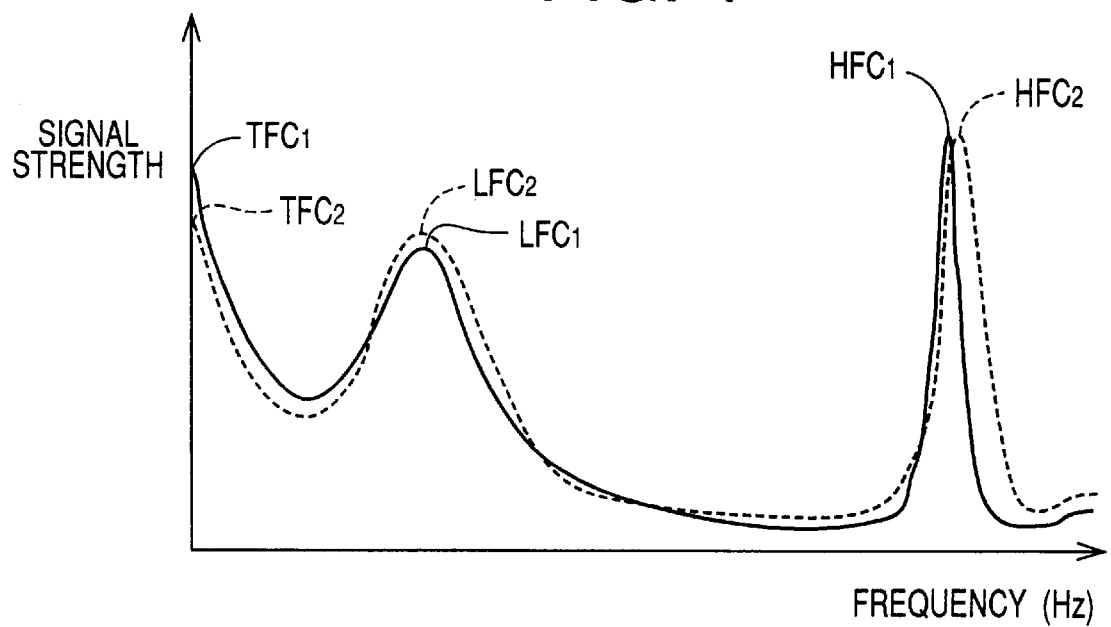
FIG. 4 is a graph showing the frequency components of the fluctuations shown in FIG. 3.

The frequency content of the fluctuations in the pulse cycle $T_{RR}$ is indicated by the solid line shown in FIG. 4. The frequency content of the fluctuations in the pulse cycle $T_{RR}$ exhibits a high frequency band and a low frequency band. The high frequency band contains a peak $HFC_1$ at a frequency that is approximately equal to the respiratory frequency of the living subject. The low frequency band contains a peak $LFC_1$ at a frequency that is approximately ¼ to ⅓ of the respiratory frequency of the living subject.

Figure 5:
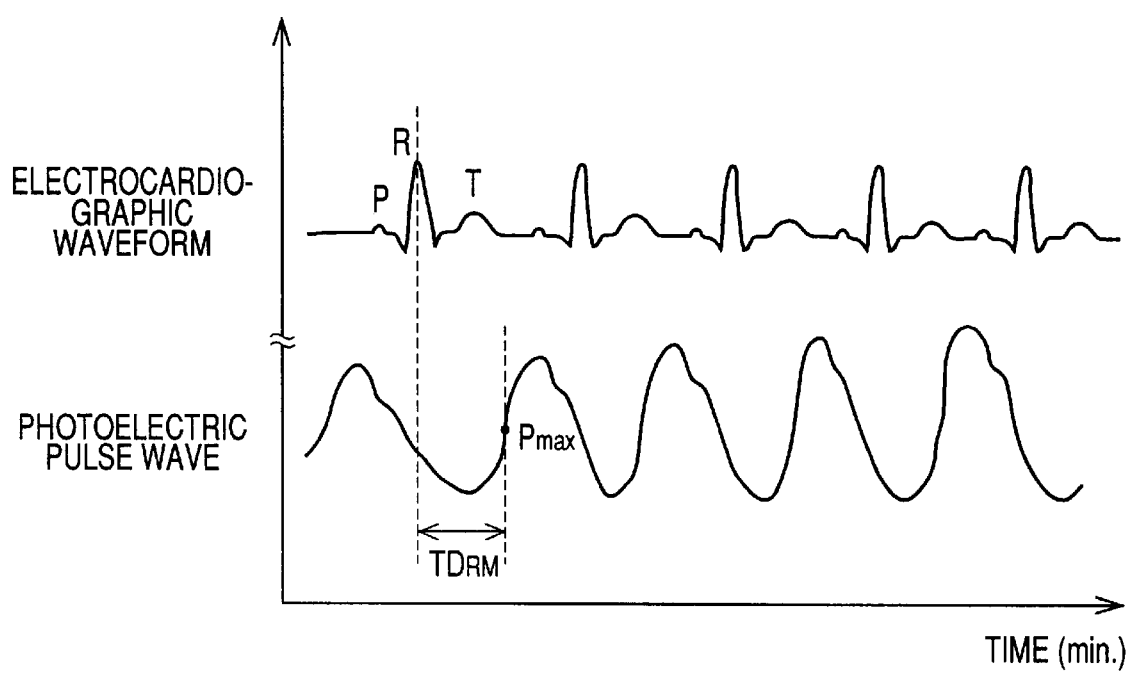
FIG. 5 is a timing chart of the electronic control device of the oxygen saturation level measuring device of FIG. 1.

A time-difference determining circuit 64 continually determines a time difference $TD_{RM}$ between predetermined periodic points on the electrocardiographic waveform and predetermined periodic points on corresponding pulse waves detected by the photoelectric pulse wave detector 12. In the preferred embodiment, the time-difference determining circuit 64 determines a time difference $TD_{RM}$ between R points on the electrocardiographic waveform and the point of maximum slope on the corresponding pulse waves detected by the photoelectric pulse wave detector 12, as shown in FIG. 5. The time difference continuously determined by the time-difference determining circuit 64 exhibits fluctuations, as shown by the plot of the reciprocal of the time difference ($1/TD_{RM}$) in FIG. 3.

A first blood pressure estimating circuit 66 continuously determines the reciprocal of the time difference $TD_{RM}$ determined by the time-difference determining circuit 64. In addition, the blood pressure estimating circuit 66 determines a propagation rate of the living subject's pulse waves based on the reciprocal of the corresponding time difference $TD_{RM}$ according to a predetermined relationship between propagation rate and the reciprocal of the time difference $TD_{RM}$. The blood pressure estimating circuit 66 then estimates the living subject's blood pressure based on the periodically determined pulse wave propagation rate according to a predetermined relationship between the living subject's blood pressure and the pulse wave propagation rate. Because the reciprocal of the time difference $TD_{RM}$ exhibits fluctuations, as shown in FIG. 3, the blood pressure estimated by the blood pressure estimating circuit 66 also exhibits fluctuations.

A second frequency analysis circuit 68 determines the frequency content of the fluctuations present in the living subject's blood pressure. The frequency analysis circuit 68 preferably uses fast Fourier transform techniques or autoregression techniques to determine the frequency content of the fluctuations present in the living subject's blood pressure.

The frequency content of the fluctuations present in the living subject's blood pressure is indicated by the dashed line in FIG. 4. The frequency content contains a high frequency band and a low frequency band. The high frequency band contains a peak $HFC_2$ at a frequency that is approximately equal to the respiratory frequency of the living subject, and the low frequency band contains a peak $LFC_2$ at a frequency that is approximately ¼ to ⅓ of the respiratory frequency of the living subject.

An autonomic nervous system evaluation circuit 70 evaluates the autonomic nervous system of the living subject based on the frequency analysis information supplied by the frequency analysis circuits 62 and 68. Specifically, the autonomic nervous system evaluation circuit 70 determines an activity level of the parasympathetic nervous system of the living subject based on the ratio of the peak $HFC_1$ to the peak $LFC_1$. In addition, the autonomic nervous system evaluation circuit 70 determines an activity level of the sympathetic nervous system of the living subject based on the ratio of the peak $HFC_2$ to the peak $LFC_2$. The autonomic nervous system evaluation circuit 70 displays the determined activity levels of the parasympathetic nervous system and the sympathetic nervous system of the living subject on display device 52.

Figure 6:
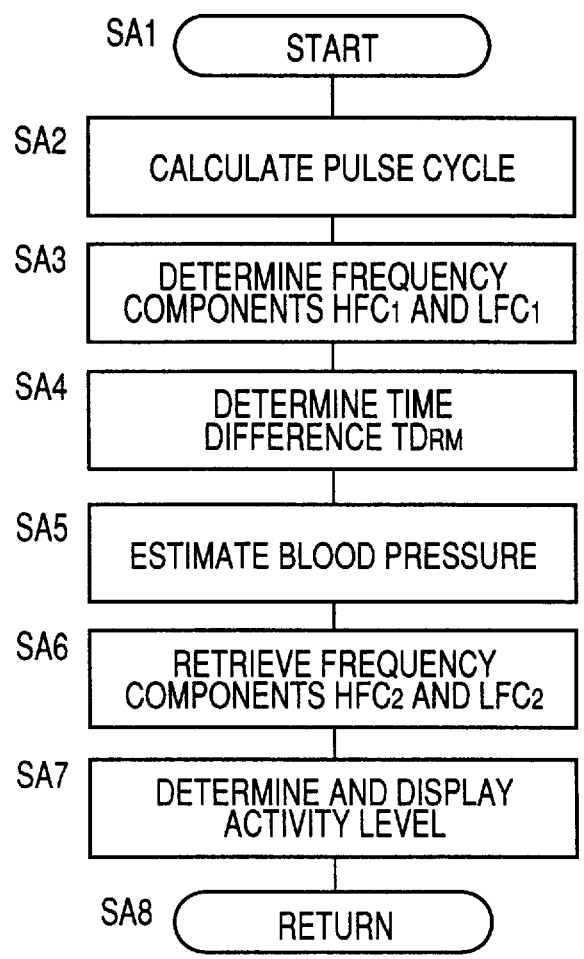
FIG. 6 is a flow chart of a preferred control routine for the oxygen saturation level measuring device of FIG. 1.

FIG. 6 shows a flow chart of a preferred control routine for the autonomic nervous system evaluation system of this invention. The routine starts at step SA1 and proceeds to step SA2, where the control system determines the pulse cycle of the living subject from the time period between successive occurrences of an R point in the electrocardiographic waveform determined by the electrocardiographic waveform determining device 48. Next, at step SA3, the control system determines the frequency components $HFC_1$ and $LFC_1$ corresponding to the peaks of the high frequency band and the low frequency band, respectively, of the fluctuations in the pulse cycle of the living subject.

Then, in step SA4, the control system determines a time difference $TD_{RM}$ between an R point on the electrocardiographic waveform and a point of maximum slope on the living subject's pulse wave. Next, in step SA5, the control system determines the reciprocal of the time difference $TD_{RM}$ determined at step SA4, determines the living subject's pulse wave propagation rate from the reciprocal of the time difference $TD_{RM}$, and estimates the living subject's blood pressure based on the determined pulse wave propagation rate. Control then continues to step SA6.

In step SA6, the control system determines the frequency components $HFC_2$ and $LFC_2$ corresponding to the peaks in the high frequency band and the low frequency band, respectively, of the fluctuations in the blood pressure estimated in step SA5. Next, in step SA7, the control system determines an activity level of the parasympathetic nervous system of the living subject based on the ratio of the peak $HFC_1$ to the peak $LFC_1$. In addition, the control system determines an activity level of the sympathetic nervous system based on the ratio of the peak $HFC_2$ to the peak $LFC_2$. The control system then displays the determined activity levels with display device 52.

The activity levels of the parasympathetic and sympathetic nervous systems of the living subject are preferably displayed on the display device 52 as a trend graph with time indicated on one axis of the graph.

The electronic control device 30, including the time-difference determining circuit 64, the blood pressure estimating circuit 66, the first and second frequency analysis circuits 62 and 68, the pulse cycle determining circuit 60 and the autonomic nervous system evaluation circuit 70, is preferably implemented using a programed general purpose computer. However, the electronic control device 30 can also be implemented using a special purpose computer, a programmed microprocessor or microcontroller and peripheral integrated circuit elements, and ASIC or other integrated circuit, a hardwired electronic or logic circuit such as a discreet element circuit, a programmable logic device such as a FPGA, a PLD, a PLA or a PAL, or the like. In general, any device in which a finite state machine capable of implementing the flow chart shown in FIG. 6 and capable of controlling the peripheral devices shown in FIGS. 1 and 2 can be used to implement the electronic control device 30 of this invention.

While this invention has been described in conjunction with the specific embodiment outlined above, it is evident that many alternatives, modifications and variations will be apparent to those skilled in the art. For example, although the autonomic nervous system evaluation system of this invention is shown in conjunction with an oxygen saturation measurement device 10, it may also be implemented with an automatic blood pressure measuring device.

In such a configuration, the cuff pulse waves detected by the automatic blood pressure measuring device are preferably used to determine the living subject's pulse wave. Thus, in an automatic blood pressure measuring device the photoelectric pulse wave detector 12 is not needed.

In addition, although a reflecting-type photoelectric pulse wave detector 12 is utilized in the preferred embodiment, a transmission-type photoelectric pulse wave detector may also be used.

Furthermore, while the preferred embodiment determines the living subject's pulse cycle $T_{RR}$ from the electrocardiographic waveform detected by the electrocardiographic waveform device 48, other means of detecting the living subject's pulse cycle may be used. For example, the living subject's pulse cycle may be determined with a pressure sensor that is mounted on a radial artery of the living subject. In addition, the living subject's pulse cycle may be measured from the cuff pulse waves that are detected in an automatic blood pressure measuring device.

In the preferred embodiment, the time difference $T_{RM}$ is calculated between an R point of the electrocardiographic waveform and a point of maximum lope of the living subject's pulse wave. However, the time difference may also be calculated from a Q point or an S point of the electrocardiographic waveform to a maximum point or minimum point on the living subject's pulse wave. In general, the time difference may be calculated between any predetermined periodic point on the electrocardiographic waveform and any predetermined periodic point on the living subject's pulse wave.

Accordingly, the preferred embodiments of the invention as set forth above are intended to be illustrative, not limiting. Various changes may be made without departing from the spirit and scope of the invention as defined in the following claims.

What is claimed is:

1. A system for evaluating an autonomic nervous system of a living subject, comprising:

a first pulse wave detection circuit that detects first pulse waves from a first portion of the living subject;

a second pulse wave detection circuit that detects second pulse waves from a second portion of the living subject;

a time-difference determining circuit that determines time differences between predetermined periodic points of the first pulse waves to predetermined periodic points of corresponding second pulse waves; and a sympathetic nervous system evaluation circuit that determines an activity level of a sympathetic nervous system of the living subject based on frequency components present in fluctuations of the time differences determined by the time-difference determining circuit.

2. The system of claim 1, further comprising a pulse cycle measuring circuit that measures a pulse cycle of the living subject from the first pulse wave detection circuit.

3. The system of claim 2, wherein said first pulse wave detection circuit comprises an electrocardiographic waveform detector that detects, as said first pulse waves, an electrocardiographic waveform of the living subject.

4. The system of claim 3, wherein the pulse cycle measuring circuit measures the living subject's pulse cycle from the electrocardiographic waveform detected by the electrocardiographic waveform detector.

5. The system of claim 2, further comprising a parasympathetic nervous system evaluation circuit that determines an activity level of a parasympathetic nervous system of the living subject based on a frequency component present in fluctuations of the pulse cycle measured by the pulse cycle measuring circuit.

6. The system of claim 5, wherein the parasympathetic nervous system evaluation circuit comprises a frequency analysis circuit that determines the frequency component of the fluctuations present in the pulse cycle of the living subject.

7. The system of claim 6, wherein the frequency analysis circuit determines a peak $HFC_1$ of a high frequency band and a peak $LFC_1$ of a low frequency band of the fluctuations of the pulse cycle of the living subject.

8. The system of claim 7, wherein the parasympathetic nervous system evaluation circuit determines the activity level of the parasympathetic nervous system of the living subject based on the ratio of the peak $HFC_1$ to the peak $LFC_1$.

9. The system of claim 1, wherein the sympathetic nervous system evaluation circuit comprises a blood pressure estimating circuit that repeatedly estimates a blood pressure of the living subject based on the time differences determined by the time-difference determining circuit.

10. The system of claim 8, wherein the sympathetic nervous system evaluation circuit determines the activity level of the sympathetic nervous system of the living subject based on the frequency component present in the fluctuations of the blood pressure estimated by the blood pressure estimating circuit.

11. The system of claim 9, wherein the sympathetic nervous system evaluation circuit comprises a frequency analysis circuit that determines the frequency components of the fluctuations present in the blood pressure of the living subject.

12. The system of claim 11, wherein the frequency analysis circuit determines a peak $HFC_2$ of a high frequency band and a peak $LFC_2$ of a low frequency band of the fluctuations of the blood pressure of the living subject.

13. The system of claim 12, wherein the parasympathetic nervous system evaluation circuit determines the activity level of the sympathetic nervous system of the living subject based on the ratio of the peak $HFC_2$ to the peak $LFC_2$.

14. The system of claim 9, wherein the blood pressure estimating circuit determines pulse wave propagation rates from the determined time differences and estimates the living subject's blood pressure based on the determined pulse wave propagation rates.

15. A system for evaluating an autonomic nervous system of a living subject, comprising:

an electrocardiographic waveform detector that detects an electrocardiographic waveform of the living subject;
a pulse wave detector that detects pulse waves of the living subject;
a pulse cycle measuring circuit that measures a pulse cycle of the living subject;
a time-difference determining circuit that determines time differences between predetermined periodic points of the electrocardiographic waveform of the living subject to predetermined periodic points of corresponding pulse waves of the living subject;
a blood pressure estimating circuit that estimates a blood pressure of the living subject based on the time differences determined by the time-difference determining device; and
an autonomic nervous system evaluation device that determines an activity level of a parasympathetic nervous system of the living subject based on frequency components present in fluctuations of the measured pulse cycle, and determines an activity level of a sympathetic nervous system of the living subject based on frequency components present in fluctuations of the estimated blood pressure.

16. The system of claim 15, wherein the electrocardiographic waveform detector comprises:

a plurality of electrocardio electrodes capable of detecting an electrocardiographic signal from the living subject when the electrocardio electrodes are in electrical contact with the living subject; and
an electrocardiographic waveform detection circuit that detects the living subject's electrocardiographic waveform based on the electrocardiographic signals detected by the electrocardio electrodes.

17. The system of claim 15, wherein the pulse wave detector comprises a blood oxygen saturation detector.

18. The system of claim 17, wherein the pulse wave detector comprises:

a housing having a top portion and an open bottom;
an attachment mechanism capable of attaching the pulse wave detector to a portion of the living subject;
a plurality of light emitters each emitting light at a different wavelength; and
a photo-detector capable of detecting light emitted by the plurality of light emitters and transmitted through the living subject.

19. The system of claim 18, wherein at least one of the plurality of wavelengths is chosen such that an absorption coefficient of oxidized hemoglobin is substantially different than an absorption coefficient of reduced hemoglobin at said one of the plurality of different wavelengths.

20. The system of claim 19 wherein the plurality of light emitters comprises:

a first light emitter emitting light at a first wavelength; and
a second light emitter emitting light at a second wavelength;
wherein the absorption coefficient of oxidized hemoglobin at the first wavelength is substantially different than the absorption coefficient of reduced hemoglobin at the first wavelength.

21. The system of claim 20, wherein the first wavelength is approximately 660 nm and the second wavelength is approximately 800 nm.

22. The system of claim 15, wherein the pulse cycle measuring circuit measures the living subject's pulse cycle from the electrocardiographic waveform detected by the electrocardiographic waveform detector.

23. The system of claim 15, wherein the time-difference determining circuit determines time differences between R points on the electrocardiographic waveform and points of maximum slope on corresponding pulse waves.

24. The system of claim 15, wherein the blood pressure estimating circuit determines pulse wave propagation rates from time differences determined by the time-difference determining circuit and estimates the living subject's blood pressure based on the determined pulse wave propagation rates.

25. The system of claim 15, wherein the autonomic nervous system evaluation device comprises:
- at least one frequency analysis circuit that determines the frequency components of the fluctuations present in the blood pressure of the living subject and determines the frequency components of the fluctuations present in the pulse cycle of the living subject; and
- an autonomic nervous system evaluation circuit that evaluates the autonomic nervous system of the living subject based on the frequency components of the fluctuations in the blood pressure and on the frequency components of the fluctuations of the pulse cycle.

26. The system of claim 25, wherein the at least one frequency analysis circuit determines a peak $HFC_1$ of a high frequency band and a peak $LFC_1$ of a low frequency band of the fluctuations of the pulse cycle of the living subject.

27. The system of claim 26 wherein the autonomic nervous system evaluation circuit determines the activity level of the parasympathetic nervous system of the living subject based on the ratio of the peak $HFC_1$ to the peak $LFC_1$.

28. The system of claim 25, wherein the at least one frequency analysis circuit determines a peak $HFC_2$ of a high frequency band and a peak $LFC_2$ of a low frequency band of the fluctuations of the estimated blood pressure of the living subject.

29. The system of claim 28, wherein the autonomic nervous system evaluation circuit determines the activity level of the sympathetic nervous system of the living subject based on the ratio of the peak $HFC_2$ to the peak $LFC_2$.

* * * * *